US00PP18337P2

(12) United States Plant Patent
Van Zanten

(10) Patent No.: US PP18,337 P2
(45) Date of Patent: Dec. 18, 2007

(54) *CHRYSANTHEMUM* PLANT NAMED 'GG GOBTW 05'

(50) Latin Name: *Chrysanthemum×morifolium*
Varietal Denomination: GG GOBTW 05

(75) Inventor: Leo Van Zanten, Oxnard, CA (US)

(73) Assignee: G + G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/395,074

(22) Filed: Mar. 31, 2006

(51) Int. Cl.
*A01H 5/00* (2006.01)

(52) U.S. Cl. ..... Plt./286

(58) Field of Classification Search ..... Plt./286
See application file for complete search history.

(56) References Cited

PUBLICATIONS

Brummit, R.K.; "The Garden"; "*Chrysanthemum* once again," Sep. 1997; pp. 662–663. (2 pages total).*

* cited by examiner

*Primary Examiner*—Kent Bell
*Assistant Examiner*—S. B. McCormick-Ewoldt

(57) ABSTRACT

A new and distinct *Chrysanthemum* plant cultivar is disclosed, characterized by small daisy type inflorescences, consistent flowering response to short days, blooming consistently after 52 days of short day length, light purple and creamy white bi-color ray florets, and a moderate branching habit.

1 Drawing Sheet

Latin name of the genus and species: *Chrysanthemum morifolium.*
Variety denomination: 'GG GOBTW 05'.

BACKGROUND OF THE INVENTION

The new cultivar 'GG GOBTW 05' was originated from a cross made by Leo Van Zanten in a planned breeding program in December 2001 between the male parent 'Tijuana' (U.S. Plant Pat. No. 9,083) and the unpatented female parent 'Mackenzie.' The new cultivar was discovered and selected by Leo Van Zanten in August 2002 in Oxnard, Calif.

Asexual reproduction of the new cultivar 'GG GOBTW 05' by vegetative cuttings was performed in Oxnard, Calif., and has shown that the unique features of this new cultivar are stable and reproduced true to type on successive generations.

SUMMARY OF THE INVENTION

The cultivar 'GG GOBTW 05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GOBTW 05.' These characteristics in combination distinguish 'GG GOBTW 05' as a new and distinct *Chrysanthemum* cultivar:

1. Small daisy type inflorescence;
2. Light purple and creamy white bi-color ray florets;
3. Moderate-branching habit;
4. And blooming consistently after 52 days of short day length.

Plants of the new cultivar 'GG GOBTW 05' are similar to plants of the male parent, 'Tijuana' in most horticultural characteristics, however plants of the new cultivar 'GG GOBTW 05' has more lavender ray florets with pale yellow bands compared to the red-purple ray florets with white bands of the parent. Additionally, the new variety 'GG GOBTW 05' has a smaller inflorescence diameter. Further, the new variety 'GG GOBTW 05' has more green foliage compared to the dark yellow-green of the parent 'Tijuana.'

Plants of the new cultivar 'GG GOBTW 05' are similar to plants of the female parent, 'Mackenzie' in most horticultural characteristics, however plants of the new cultivar 'GG GOBTW 05' are bi-color ray florets compared to the single color purple ray florets of the female parent. Also, 'GG GOBTW 05' has yellow disc florets compared to the yellow-green disc florets of the female parent. Finally, the ray florets of the new cultivar 'GG GOBTW 05' are a much lighter purple than the dark purple ray florets of the female parent.

In comparison to the commercially available variety 'New Yoorleans' (U.S. Plant Pat. No. 11,215), the bi-color ray florets of 'GG GOBTW 05' are lavender and pale yellow compared to the dark red-purple and white bi-color ray florets of the comparable variety. Additionally, the new variety 'GG GOBTW 05' is smaller in both height and plant spread. Further, the new variety 'GG GOBTW 05' has more true green foliage and a smaller inflorescence diameter than the comparable variety.

BRIEF DESCRIPTION OF THE PHOTOGRAPH

The accompanying photograph in FIG. 1 illustrates in full color a typical plant of 'GG GOBTW 05' grown in a 6.5-inch container. Five cuttings were used in the pot, planted late October and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG GOSUN 05' plants grown in Oxnard, Ventura County, Calif., during the winter months. The growing temperature in the greenhouse ranged from 67° F. and 78° F. Measurements and numerical values represent averages of typical flowering types.

Botanical classification: *Chrysanthemum morifolium* cultivar 'GG GOBTW 05.'
Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 26 cm.
Plant spread: Approximately 30 cm.
Growth rate: Moderate.
Branching characteristics: Moderate branching.
Length of lateral branches: Approximately 20 cm.
Number of leaves per lateral branch: Approximately 16.
Age of plant described: Approximately 98 days.

FOLIAGE

Leaf:
*Arrangement.*—Alternate single.
*Average length.*—Approximately 7 cm.
*Average width.*—Approximately 5.5 cm.
*Shape of blade.*—Ovate.
*Apex.*—Acuminate.
*Base.*—Attenuate.
*Attachment.*—Stalked.
*Margin.*—Palmately lobed, sinuses between lateral lobes parallel to divergent.
*Texture of top surface.*—Lightly pubescent.
*Texture of bottom surface.*—Lightly pubescent.
*Leaf internode length.*—Approximately 1.9 cm.
*Color.*—Young foliage upper side: Near Green 137A. Young foliage under side: Near Green 138B. Mature foliage upper side: Near Green 137A. Mature foliage under side: Near Green 137C.
*Venation.*—Type: Palmately net. Venation color upper side: Near Green 137C. Venation color under side: Near Green 137C.

Petiole:
*Average length.*—Approximately 2 cm.
*Color.*—Near Green 137C.
*Diameter.*—Approximately 0.2 cm.

BLOOM

Inflorescence:
*Flowering habit.*—Induced by darkness period greater than 13.5 hours, approximately 52 days of appropriate day length required to induce and develop blooms.
*Inflorescence form.*—Daisy.
*Number of inflorescences per lateral branch.*—Approximately 7.
*Inflorescence diameter.*—Approximately 5.5 cm.
*Inflorescence depth.*—Approximately 1.7 cm.
*Inflorescence longevity on plant.*—Approximately 35 to 42 days.
*Persistence.*—Persistent.
*Fragrance.*—None detected.

Ray florets:
*Appearance.*—Matte.
*Texture.*—Smooth.
*Average number of ray florets per inflorescence.*—23.
*Number of whorls.*—Approximately 2.
*Shape.*—Oblanceolate.
*Aspect.*—Flat.
*Margin.*—Entire.
*Apex.*—Obtuse.
*Length.*—Approximately 1.7 cm.
*Width.*—Approximately 0.7 cm.
*Color.*—Upper surface at first opening: Near Purple 78C at apex of the ray floret, blending into Yellow-White 158D at base. Upper surface at maturity: Near Purple 78A at apex of the ray floret, blending into Yellow-White 158D at base. Upper surface at fading: Near Purple-Violet 80D at apex of the ray floret, blending into Yellow-White 158D at base. Under surface at first opening: Near Purple 78C at apex of the ray floret and blending into Yellow-White 158D at base. Under surface at maturity: Near Purple 78C at apex of the ray floret and blending into Yellow-White 158D at base. Under surface at fading: Near Purple-Violet 80D at apex of the ray floret and blending into Yellow-White 158D at base.

Disc florets:
*Appearance.*—Matte.
*Texture.*—Smooth.
*Average number of florets per disc.*—Approximately 180.
*Shape.*—Cylindric.
*Apex.*—Obtuse.
*Average length.*—Approximately 0.2 cm.
*Average width.*—Approximately 0.1 cm.
*Color.*—At first opening: Near Yellow-Green 145A. At maturity: Near Yellow 9A. At fading: Near Greyed-Orange 177D.

Peduncle:
*Length.*—At terminal end (shortest): Approximately 3.6 cm. At lateral end (longest): Approximately 4.2 cm.
*Angle to stem.*—Acute.
*Strength.*—Moderate.
*Color.*—Near Green 138A.
*Habit.*—Upright.
*Diameter.*—Approximately 0.1 cm.
*Surface texture.*—Lightly pubescent.

Inflorescence bud:
*Length.*—Approximately 0.4 cm.
*Diameter.*—Approximately 0.6 cm.
*Form.*—Globular.
*Color.*—Near Green 138B.

Involucral bracts (phyllaries):
*Appearance.*—Matte.
*Texture.*—Lightly pubescent.
*Number.*—Approximately 22.
*Shape.*—Ovate.
*Margin.*—Entire.
*Apex.*—Acute.
*Length.*—Approximately 0.5 cm.
*Width.*—Approximately 0.3 cm.
*Color.*—Upper side: Near Green 137A. Under side: Near Green 137B.

REPRODUCTIVE ORGANS

Ray florets:

*Number of pistils per floret.*—1.
*Stigma shape.*—2 branched.
*Stigma color.*—Near Yellow 9A.
*Style color.*—Near Yellow-Green 145B.
*Style length.*—Approximately 0.3 cm.
*Stamens.*—Absent.

Disc florets:

*Number of pistils per floret.*—1.
*Stigma shape.*—Cylindric.
*Stigma color.*—Near Yellow 9A.
*Style length.*—Approximately 0.2 cm.
*Style color.*—Near Yellow-Green 149C.
*Number of stamens per floret.*—Approximately 5.
*Anther shape.*—tubular.
*Anther color.*—Near Yellow 9A.
*Pollen color.*—Near Yellow 9A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG GOBTW 05' as herein illustrated and described.

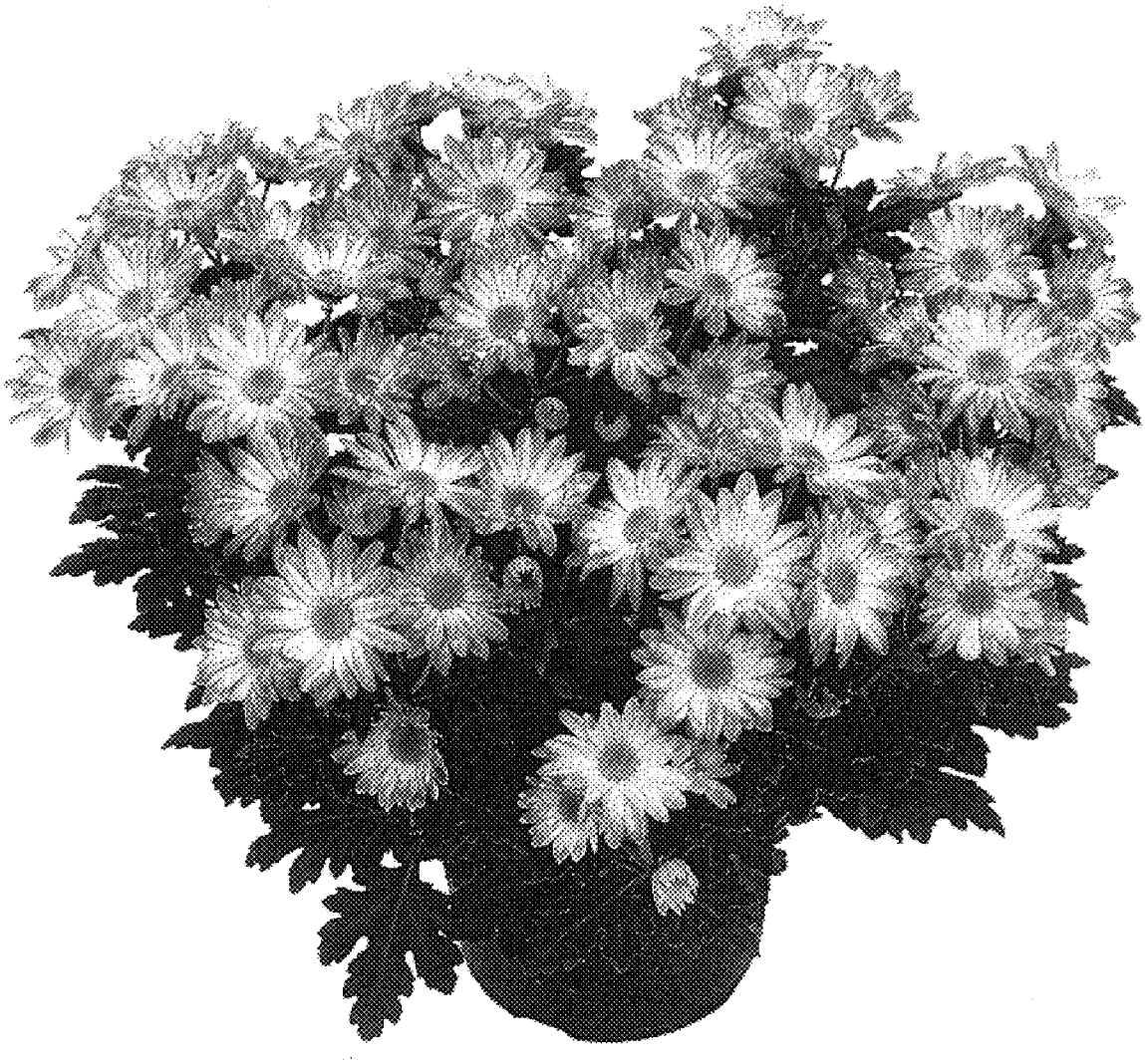

* * * * *